United States Patent [19]

Kliment et al.

[11] Patent Number: 4,729,914

[45] Date of Patent: Mar. 8, 1988

[54] HYDROPHILIC COATING AND SUBSTRATE COATED THEREWITH

[75] Inventors: Charles K. Kliment, Princeton; George E. Seems, Pennington, both of N.J.

[73] Assignee: Tyndale Plains-Hunter Ltd., Princeton, N.J.

[21] Appl. No.: 56,338

[22] Filed: May 22, 1987

Related U.S. Application Data

[63] Continuation of Ser. No. 814,906, Dec. 30, 1985, abandoned.

[51] Int. Cl.$^4$ .................. B32B 7/04; B32B 27/40; B32B 31/06
[52] U.S. Cl. .................. 428/36; 128/132 R; 351/160 R; 428/420; 428/423.1; 428/424.2; 604/96; 604/264
[58] Field of Search .................. 428/420, 424.2, 423.1, 428/500, 36; 128/132 R; 604/96, 264; 351/160 R

[56] References Cited

U.S. PATENT DOCUMENTS

| | | | |
|---|---|---|---|
| 3,092,512 | 6/1963 | Magat | 428/424.2 |
| 4,119,094 | 10/1978 | Micklus et al. | 128/132 R |
| 4,175,161 | 11/1979 | Fogle et al. | 428/500 |
| 4,487,808 | 12/1984 | Lambert | 428/423.1 |

FOREIGN PATENT DOCUMENTS

2122510A  1/1984  United Kingdom ............ 128/132 R

*Primary Examiner*—Thomas J. Herbert
*Attorney, Agent, or Firm*—Ratner & Prestia

[57] ABSTRACT

An article having a lower coefficient of friction in the wet state is produced by applying to a substrate an adherent isocyanate coating followed by a second coating of polyvinylpyrrolidone copolymerized with a minor amount of an ethylenic monomer having active hydrogens and curing the so-coated substrate to effect reaction between the active hydrogens and isocyanate groups. The article is useful in the manufacture of medical devices for insertion in the body.

15 Claims, No Drawings

HYDROPHILIC COATING AND SUBSTRATE COATED THEREWITH

This application is a continuation of application Ser. No. 814,906, filed Dec. 30, 1985, now abandoned.

This invention relates to hydrophilic coatings having a lower coefficient of friction in the wet state than in the dry state. The invention also pertains to a process of preparing said coatings and to coated articles produced therefrom.

Hydrophilic coatings which absorb aqueous fluids to form hydrated coatings having a lower coefficient of friction than the precursor dry coatings are known in the art. Such coatings have various uses, particularly, in the field of medicine. For instance, the coatings can be applied to devices or instruments intended for insertion into body tissues or cavities. On contact with body fluids or wet mucous membranes, the coatings undergo hydration becoming very slippery owing to the lowering of the coefficient of friction. In this condition, the coated objects can be easily inserted or removed from the body without causing damage or discomfort to the patient. In the dry state, however, the coated objects are not slippery and can readily be grasped by the hand and generally handled in a normally convenient manner.

An example of the hydrophilic coatings aofresaid is set forth in British Pat. No. 1,600,963 to Biomedical Medical Products, Inc. According to the patent, the coatings comprise a polyvinylpyrollidone-polyurethane interpolymer. They are produced by first applying a polyisocyanate and a polyurethane in a solvent to a suitable substrate after which the solvent is evaporated, leaving a surface layer of polyurethane with unreacted isocyanate groups. The so-treated substrate is then coated with polyvinylpyrollidone to form the polyvinylpyrollidone-polyurethane interpolymer.

Although exhibiting increased lubricity in the wet state, the hydrophilic coatings of the British patent have not proved entirely satisfactory. This is not surprising, since according to later issued U.S. Pat. No. 4,487,808, which discusses these coatings, their manufacture is too complicated for large-scale production and moreover, the coatings were found to be susceptible to cracking. Another drawback is the presence of unreacted polyvinylpyrollidone which can leach out of the coating during use.

Hydrophilic polyvinylpyrrolidone coatings have now been discovered which are an improvement over those of the prior art aforesaid and the provision of said coatings, substrates coated therewith and vinyl pyrrolidone polymers used in making the said coatings constitute the principal object and purpose of the invention. Other objects and purposes will be made manifest subsequently herein.

The hydropholic coatings of the invention are produced by applying to a substrate having free isocyanate groups, a copolymer of vinylpyrrolidone with an ethylenically unsaturated monomer containing active hydrogen capable of reacting with the free isocyanate groups attached to the substrate. Chemical reaction is then caused to take place between the isocyanate groups and the reactive hydrogens in the copolymer thereby firmly binding the latter to the substrate. So far as can be ascertained, polyvinylpyrrolidone is not leached from the herein coatings when they are contacted with polar solutions such as alcohol or aqueous media. It is believed that the strong chemical union between the isocyante groups in the substrate and the reactive hydrogens in the ethylenic monomer prevents leaching of the polyvinylpyrrolidone. In the reference coatings, on the other hand, the polyvinylpyrrolidone is apparently rather feebly bound to the polyurethane/polyisocyanate interlayer on the substrate. This is thought to be due to the polyvinylpyrrolidone being bound to the interlayer by physical rather than chemical forces; that is, there is no chemical reaction of polyvinylpyrrolidone with an isocyanate. But whatever the explanation, the fact remains that the reference coatings are subject to leaching of the polyvinylpyrrolidone.

The N-vinylpyrrolidone copolymers of the invention are obtained by the copolymerization of N-vinylpyrrolidone and an ethylenically unsaturated monomer having active hydrogens of the type that react with an organic isocyanate. The polymerization is carried out in the known manner. Typically, the monomers are dissolved in a solvent containing a polymerization initiator and the solution heated to mildly elevated temperatures, generally in the range of about 35° C. to about 100° C. Completion of the reaction is effected by heating for a few hours, usually about 2 to 8 hours. The copolymer is recovered by removal of the solvent which is desirably an organic liquid boiling in the range of about 35° C. to about 130° C. Examples of such solvents include methyl alcohol, ethyl alcohol, tetrahydrofuran, isopropyl ether, chloroform, methylene chloride, acetone, methyl ethyl ketone and the like. Suitable polymerization initiators include any source of free radicals such as for example, azobisisobutyronitrile, peroxygen compounds such as hydrocarbon peroxide diisopropyl percarbonate, benzoyl peroxide and the like.

As previously pointed out herein, the N-vinylpyrrolidone copolymers of the invention contain active hydrogens which react with the isocyanate groups in the substrate. This results in a chemical bonding to the substrate of coatings prepared from the N-vinylpyrrolidone copolymers. The reactive hydrogens are in the form of functional substituents attached to an ethylenically unsaturated monomer. Generally speaking, the amount of ethylenic monomer that is required to properly bond the copolymer to the substrate is relatively minor compared to the N-vinylpyrrolidone which constitutes the major portion of the copolymer. A satisfactory numerical monomer ratio for preparing the copolymers is about 2% to about 10% ethylenic monomer and about 90% to about 98% N-vinylpyrrolidone.

The active hydrogens in the monomer typically occur in such functional entities as —OH, =NH, —COOH and —SH. Examples of the ethylenic monomers aforesaid include allyl alcohol, methallyl alcohol, acrylic acid and lower hydroxyalkyl esters thereof such as 2-hydroxyethyl acrylate, methacrylic acid and lower hydroxyalkyl esters thereof such as 2-hydroxyethyl methacrylate, 2-hydroxyethylthioacrylate, N-hydroxyethylacrylamide, 2-butene-1-carboxylic acid, 2-hydroxyethyl ester and the like.

The substrate may be any material of the requisite structural integrity but is commonly a metal or a polymer such as polyurethane, vinyl resin as exemplified by polyvinyl chloride, a polyacrylate, such as polymethylmethacrylate, a polycarbonate, a polyester such as polyethylene terephthalate, polybutylene terephthalate, polytetramethylene terephthalate as well as various rubbery polymers such as polyisoprene and latex. Isocyanate groups are applied to the substrate by coating it with a solution of a polyisocyanate by means of known coating techniques such as dipping, spraying or the like and then evaporating the solvent, preferably by air drying leaving a film of the polyisocyanate on the surface of the surface. Examples of polyisocyanates are polyphenyl isocyanate, 4,4-diphenylmethane diisocyanate and 2,4-toluene diisocyanate. Desirably, the polyisocyanate coating solution contains a film forming material to enhance toughness and adherency of the dried polyisocyanate coating. More desirably, however, the coating is formed from a polyurethane prepolymer of the type obtained by condensing a resin having active hydrogens with an excess of a polyisocyanate. Such isocyanate terminated prepolymers are well known in the polyurethane art and their description including preparation and uses as coating materials are documented extensively in the patent and technical literature; cf. "The Development and Use of Polyurethane Products" by E. N. Doyle (1971) published by McGraw-Hill, Inc.

Illustrative of the resins used in preparing polyurethane prepolymers include polyether polyols such as polyethylene glycol, polypropylene glycol, polylactones and the like. A particularly large class of active hydrogen polyols are the polyol polyesters which can be generally described as the reaction product of a polycarboxylic acid and a polyhydroxy compound. Examples of the polyhydroxy compounds include ethylene glycol, propylene glycol, tetramethylene glycol, glycerine, and the like. The polycarboxylic acid is commonly a dicarboxylic acid, particularly an aliphatic acid of 5 to 8 carbons atoms, adipic acid being a typical member that is often employed in the manufacture of polyol polyesters. In some instances, a small amount of a low molecular weight diol as for example, 1,4-butanediol may be added to the polyol resin in the preparation of the herein polyurethane prepolymers. A preferred isocyanate terminated prepolymer derived from a polyether polyol is obtained by reacting a major amount of a polyoxyethylene glycol having a molecular weight of from about 1000 to about 8000 or mixtures thereof, a minor amount of diethylene glycol and excess polyisocyanate such as DESMODUR W$^R$ (Mobay). Exemplary polyoxyethylene glycols are the various carbowaxes available in a range of molecular weights from the Union Carbide Corporation. Representative carbowaxes are PEG (CARBOWAX 1450®) and PEG (CARBOWAX 8000®) in which numbers refer to molecular weights. Such simple diols function as chain extenders and modifiers. For further details on the manufacture and use of urethane polymers, see the aforecited "The Development and Use of Polyurethane Products".

The isocyanate is applied to the substrate in a solvent that does not react with isocyante groups. Suitable solvents include alkyl chlorides such as methylene chloride, ethylene chloride; ethyl acetate, acetone, methyl ethyl ketone and alkyl ethers. The solvent is desirably a liquid at ordinary temperatures and pressures.

The isocyanate solution can be of any concentration but is conveniently applied to the substrate at a solids content of from about 2% to 15% by weight, generally at about 3% to about 7%. Application of the isocyanate solution is by the usual procedures, commonly by dipping or spraying. The coating is air-dried to effect evaporation of solvent; normally, drying times are from about 5 to 60 minutes. Adherence of the isocyanate to certain substrates such as rubber latex can be improved by pretreatment with a swelling solvent or the isocyanate can be dissolved in a solvent that exhibits a swelling action on the surface.

After evaporation of the isocyanate solvent, there remains a strong, adherent film of the isocyanate on the surface of the substrate. This is then overcoated by dipping or spraying with a solution of the N-vinylpyrrolidone copolymer and the so-coated substrate subjected to air drying until the solvent is evaporated. The solvent for the N-vinylpyrrolidone copolymer is desirably an organic liquid which is relatively easy to evaporate at room or slightly elevated temperatures. Exemplary solvents for the copolymer are chlorinate alkanes such as dichloroethane and methylene chloride. Following removal of the solvent, there remains on the isocyanate coated substrate, an outer film of the N-vinylpyrrolidone copolymer.

The coated substrated aforesaid is heated to curing temperatures, preferably between about 50° C. and 110° C., whereby the free isocyanate groups in the inner coating react with the active hydrogen in the ethylenic monomer units of the N-vinylpyrrolidone copolymer. This chemical union firmly binds the outer polyvinylpyrrolidone to the inner isocynate coating. On contact with aqueous media, the outer surface of the substrate undergoes hydration with concomitant increase in the coefficient of friction of the wetted surface. There was no leaching of ingredients from the coating into the aqueous media.

The coated substrates of the invention are useful as catheters, implant devices, contact lenses, peristaltic pump chambers, condoms, arteriovenous shunts, gastroenteric feed tubes, endotracheal tubes and the like.

The invention is illustrated further by the following examples in which the quantities are parts by weight.

EXAMPLE 1

One hundred eleven parts (111.0) of N-vinylpyrrolidone and 2.06 parts of 2-hydroxyethyl methacrylate were dissolved in 300 parts of methyl alcohol in a reaction vessel, equipped with a stirrer and a reflux condenser. The reaction mixture was brought to 68° C.-69° C. under nitrogen, and 0.5 parts of azobisisobutryonitrile (polymerization initiator) were added.

The reaction mixture was refluxed for 6 hours under constant stirring. The conversion to polymer was found to be 99.2%.

EXAMPLE 2

The polymer solution from Example 1 was stripped of 200 parts of methyl alcohol at 40° C. under vacuum. Two hundred parts (200) of dimethyl formamide were added to the solution and the remaining alcohol was stripped at 40° C. under vacuum. The viscosity of the final solution of the polymer in DMF was 920 cP at 25° C.

EXAMPLE 3

One hundred twenty (120) parts of N-vinylpyrrolidone and 4.6 parts of allyl alcohol were dissolved in 200 parts of tetrahydrofuran in a reaction vessel, equipped with a stirrer and a reflux condenser. The reaction mixture was heated to 40° C. under a nitrogen blanket, and 0.6 parts of diisopropyl percarbonate were added. The reaction was allowed to proceed at 40° C. for 5 hours.

Conversion to polymer was found to be 99.1%, viscosity of the solution was 550 cP at 25° C.

EXAMPLE 4

Eighty-six (86) parts of N-vinylpyrrolidone and parts of hydroxypropyl acrylate were dissolved in 160 parts of ethyl alcohol and 60 parts of acetone in a reaction vessel equipped with a stirrer and a reflux condenser. The reaction mixture was brought to 40° C. under a nitrogen blanket, 0.5 parts of diisopropyl percarbonate were added and the reaction was carried on for 6 hours.

Conversion to polymer was found to be 98.5%, and the viscosity of the solution was 480 cP at 25° C.

EXAMPLE 5

A latex tubing (an urological catheter) was dipcoated in a solution containing 2 parts of Pellethane 2363 (Dow) and 1 part of diisocyante prepolymer, containing 20%–22% free isocyanate (Boscodur 4 by Bostik), in 97 parts of dichloroethane. The solution was air-dried for 10 minutes, and the coated tube was dip-coated in a polymer solution from Example 2 and allowed to air-dry for 10 minutes. The coatings were cured at 100° C. for 20 minutes.

The final coating had a kinetic coefficient of friction in wet state of 0.024, as measured according to ASTM D-1894-75 method.

EXAMPLE 6

A prepolymer was prepared by reacting 48.79 parts of CARBOWAX 1450$^R$ (Union Carbide), 7.73 parts of diethylene glycol and 43.48 parts of methylene-bis(dicyclohexylisocyanate) (DESMODUR®W, Mobay) with 0.2 parts of stannous octoate (reaction catalyst).

The polymer was dissolved at 5% solids in chloroform.

EXAMPLE 7

A prepolymer was prepared by reacting 76.10 parts of CARBOWAX 8000® (Union Carbide), 2.59 parts of diethylene glycol and 21.31 parts of DESMODUR®W (Mobay) with 0.2 parts of stannous octoate.

The polymer was dissolved as 3% solids in dimethyl formamide.

EXAMPLE 8

A PVC extruded tubing was dip-coated in a prepolymer solution of Example 6 and air-dried for 5 minutes. Then it wa dip-coated in one part of polymer solution of Example 3 and 2 parts of dichloroethane, and air-dried for 5 minutes. Both coatings were cured at 80° C. for one hour.

The final coating had excellent adhesion to the substrate, which did not diminish after prolonged swelling in water at 37° C., exhibited high slipperiness and now low-molecular weight compounds leached out of it.

EXAMPLE 9

A polyurethane (Pellethane 2363, Dow) extruded tubing was dip-coated, using the prepolymer solution from Example 7, and air-dried for 10 minutes. The outer coating was dip-coated, using the polymer solution from Example 4, air-dried for 10 minutes and both coatings were cured at 100° C. for 20 minutes.

The final coating in swollen state had the kinetic coefficient of friction of 0.031, and all the other advantages as mentioned in Example 8.

What is claimed is:

1. An article having thereon a coating which swells in the presence of aqueous media with concomitant reduction in the coefficient of friction, the said article being produced by:

applying to a substrate, an adherent coating having free isocyanate groups;

applying to the so-coated substrate a second coating of a vinyl copolymer having a major polymeric component derived from N-vinylpyrrolidone and a minor polymeric component derived from an ethylenically unsaturated monomer containing reactive hydrogens, and heating the coated substrate to curing temperatures to effect reaction between the active hydrogens and isocyanate groups thereby chemically binding the copolymer coating to the adherent isocyanate coating.

2. The article of claim 1 wherein the adherent isocyanate coating is a diisocyanate terminated prepolymer, produced by reacting a resin having reactive hydrogens with excess diisocyanate.

3. The article of claim 1 wherein the resin is a polyether polyol.

4. The article of claim 1 wherein the ethylenic monomer is 2-hydroxyethyl methacrylate.

5. The article of claim 1 wherein the ethylenic monomer is hydroxypropyl acrylate.

6. The article of claim 1 wherein the ethylenic monomer is allyl alcohol.

7. The article of claim 1 wherein the substrate is a polymer.

8. The article according claim 1 wherein the substrate is a catheter.

9. The article according to claim 1 wherein the substrate is an implant device.

10. The article according to claim 1 wherein the substrate is a contact lens.

11. The article according to claim 1 wherein the substrate is a peristaltic pump chamber.

12. The article according to claim 1 wherein the substrate is a condom.

13. The article according to claim 1 wherein the substrate is an arteriovenous shunt.

14. The article according to claim 1 wherein the substrate is a gastroenteric feed tube.

15. The article according to claim 1 wherein the substrate is an endotracheal tube.

* * * * *

UNITED STATES PATENT AND TRADEMARK OFFICE
CERTIFICATE OF CORRECTION

PATENT NO. : 4,729,914
DATED : March 8, 1988
INVENTOR(S) : Charles K. Kliment and George E. Seems It is certified that error appears in the above—identified patent and that said Letters Patent is hereby corrected as shown below:

Column 6, line 34 delete "1" and insert --2--.

Signed and Sealed this

Ninth Day of August, 1988

Attest:

DONALD J. QUIGG

*Attesting Officer*  *Commissioner of Patents and Trademarks*